United States Patent [19]

Tashiro et al.

[11] Patent Number: 4,514,403
[45] Date of Patent: Apr. 30, 1985

[54] HYDROURACIL COMPOUNDS

[75] Inventors: Chiaki Tashiro, Fukuoka; Takeshi Kawakita, Oita; Ichiro Horii, Fukuoka; Koretake Anami, Oita, all of Japan

[73] Assignee: Yoshitomi Pharmaceutical Industries Ltd., Japan

[21] Appl. No.: 303,269

[22] Filed: Sep. 17, 1981

[30] Foreign Application Priority Data

Sep. 17, 1980 [JP] Japan ............................. 55/129816

[51] Int. Cl.³ .................. A61K 31/505; C07D 401/04
[52] U.S. Cl. .................................. 514/274; 544/312
[58] Field of Search ....................... 544/312; 542/445; 424/251

[56] References Cited

U.S. PATENT DOCUMENTS 4,216,216 8/1980 Weber et al. ........................ 544/312

FOREIGN PATENT DOCUMENTS 55-24155 2/1980 Japan .

OTHER PUBLICATIONS

Tashiro et al., Chemical Abstracts, 93, 186387e, (1980).

Primary Examiner—Paul M. Coughlan, Jr.
Attorney, Agent, or Firm—Sughrue, Mion, Zinn, Macpeak and Seas

[57] ABSTRACT

A hydrouracil compound of the formula:

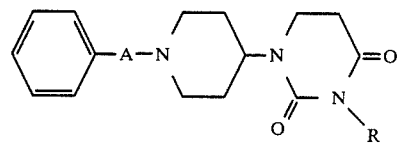

or a pharmaceutically acceptable acid addition salt thereof, wherein A represents —CH=CH—CH₂— or —CH₂CH₂—, and R represents hydrogen or methyl. Such compounds are useful as analgesics.

6 Claims, No Drawings

HYDROURACIL COMPOUNDS

This invention relates to novel and therapeutically valuable hydrouracil compounds of the formula:

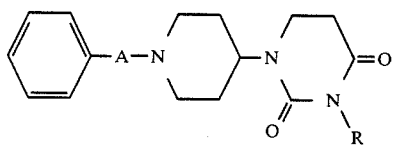 (I)

and pharmaceutically acceptable acid addition salts thereof, wherein A represents —CH=CH—CH$_2$— or —CH$_2$CH$_2$—, and R represents hydrogen or methyl.

The compounds of the present invention are useful as analgesics which have a quite new mechanism of action.

The compounds of formula (I) can be produced by the following Method I or II.

Method I

Reaction of a compound of the formula:

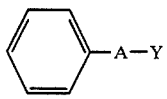 (II)

wherein A is as defined above, and Y represents a reactive atom or group such as halogen (Cl or Br), lower alkylsulfonyloxy (e.g. methylsulfonyloxy or ethylsulfonyloxy) or arylsulfonyloxy (e.g. phenylsulfonyloxy or p-tolyl-sulfonyloxy), with a compound of the formula:

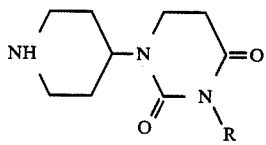 (III)

wherein R is as defined above.

The reaction is usually carried out in an inert solvent such as water, methanol, ethanol, isopropanol, acetone, methyl ethyl ketone, methyl isobutyl ketone, tetrahydrofuran, dioxane, 1,2-dimethoxyethane, benzene, toluene or a mixture thereof, in the presence of an acid acceptor such as potassium carbonate, at a temperature of from about 0° C. to the boiling point of the solvent employed, for a period of from several hours to ten-odd hours.

Method II

Reaction of a compound of the formula:

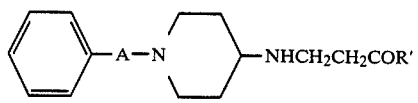 (IV)

wherein A is as defined above, and R' is lower alkoxy (e.g. methoxy or ethoxy), amino or lower alkylamino (e.g. methylamino or ethylamino), with urea, a carbonic acid derivative (e.g. urethane, ethyl chloroformate, diethyl carbonate or phosgene), isocyanic acid or methyl isocyanate.

The reaction is usually carried out (1) when urea or a cabonic acid derivative is reacted, by heating in the absence or presence of an inert solvent (e.g. water, acetic acid, ethylene glycol monomethyl ether or chloroform) or an acid acceptor (e.g. triethylamine or pyridine) at about 100°–150° C., (2) when isocyanic acid is reacted, by dissolving a compound (IV) in a dilute acid (e.g. dilute hydrochloric, dilute sulfuric or 80% acetic acid), adding an alkali isocyanate and stirring the resulting mixture at room temperature or under reflux, and (3) when methyl isocyanate is reacted, by stirring under cooling in an inert solvent (e.g. methanol, ethanol, benzene, toluene, chloroform, dioxane or tetrahydrofuran) and heating to the boiling point of the solvent employed in the presence of an acid, if necessary.

The compounds of formula (I) can form pharmaceutically acceptable acid addition salts with various inorganic and organic acids such as hydrochloric, hydrobromic, oxalic, maleic, fumaric, citric, tartaric, methanesulfonic and p-toluenesulfonic acids.

As analgesics, there are (1) centrally acting analgesics, e.g. pentazocine, (2) antipyretic analgesics, e.g. aminopyrine and (3) antiinflammatory analgesics, e.g. indomethacine and mefenamic acid. These drugs are widely used in painful diseases. Centrally acting analgesics, although effective in severe pain such as postoperative pain and carcinomatous pain, are shown to have drawbacks such as respiratory suppression and acquisition of dependence, and so their use is limited. On the other hand, antiinflammatory analgesics have been used widely in the field of painful diseases since they are effective and easy to be used. Effectiveness of antiinflammatory analgesics, however, is more evident in inflammatory pain such as pain after tooth extraction, traumatic pain and lumbago than in severe pain such as postoperative pain and carcinomatous pain, and does not yet cover the whole region of painful diseases.

The compounds of the present invention show potent central analgesic activities and do not show formation of tolerance and physical dependence even by repeated administration.

PHARMACOLOGICAL PROPERTIES

Test Compounds:

A: 1-(1-cinnamyl-4-piperidyl)-3-methyl-hydrouracil hydrochloride

B: 1-(1-cinnamyl-4-piperidyl)hydrouracil hydrochloride

C: 1-(1-phenethyl-4-piperidyl)-3-methyl-hydrouracil hydrochloride

D: 1-(1-phenethyl-4-piperidyl)hydrouracil hydrochloride

Analgesic Activity:

(1) Methods

Phenylquinone writhing test, electric stimuli test, tooth pulp nociception test, hot plate test and AgNO$_3$ arthritis test were performed according to the methods described by Y. Marayama et al. in "Arzneimittel-Forschung", 28 (11), 2102–2107 (1978), and bradykinin nociception test was performed by the method described by G. F. Blane in "Journal of Pharmacy and Pharmacology", 19, 367–373 (1967).

(2) Results

The results are summarized in Table I.

TABLE I

| Test Compound | Phenylquinone Writing Test ED$_{50}$ mg/kg mice | | Electric Stimuli Test ED$_{50}$ mg/kg mice | | Tooth Pulp Nociception Test IT$_{100}$ mg/kg rabbits | Hot Plate Test ED$_{50}$ mg/kg rats | Bradykinin Nociception Test ED$_{50}$ mg/kg rats | | AgNO$_3$ Arthritis Test ED$_{50}$ mg/kg rats |
|---|---|---|---|---|---|---|---|---|---|
| | p.o. | s.c. | p.o. | s.c. | i.v. | s.c. | p.o. | s.c. | s.c. |
| A | 17 | 1 | 200 | 23 | 3.7 | 10 | 40 | 4 | 7 |
| B | 18 | 7.8 | 200 | 40 | 7 | 90 | 100 | 10 | 25 |
| C | 5 | 1.5 | 220 | 50 | 4 | 10 | 400 | 70 | 45 |
| D | 4 | 2.5 | 220 | 100 | 14 | 200 | — | 25 | 90 |
| Tramadol | 11 | 1.5 | 23 | 12 | 5 | 50 | 50 | 70 | 17 |
| Pentazocine | 18 | 1.3 | 178 | 23 | 4.5 | 30 | 100 | 8 | 10 |
| Morphine | 2.1 | 0.4 | 17 | 3 | 0.6 | 4 | 50 | 6 | 0.8 |
| Aminopyrine | 92 | 16 | 315 | 100 | 55 | — | — | 30 | 170 |

Then, the analgesic activity in a low dose was determined. The results are summarized in Table II.

TABLE II

| Method | Animals | Dose (mg/kg) | Route | Inhibition (%) of Occurrence of Pain | | | |
|---|---|---|---|---|---|---|---|
| | | | | A | Tramadol | Pentazocine | Morphine |
| Phenylquinone Writhing Test | mice | 0.5 | s.c. | 48 | 12 | 15 | 78 |
| Tooth Pulp Nociception Test* | rabbits | 2.5 | i.v. | 75 | 67 | 44 | 186 |
| Bradykinin Nociception Test | rats | 2.5 | s.c. | 38 | 18** | 13 | 17 |
| AgNO$_3$ Arthritis Test | rats | 5 | s.c. | 42 | 0 | 33 | 100 |

*increasing rate in threshold
**inhibition (%) when 25 mg/kg was injected

The potencies of the test compounds presented in Table II are summarized in Table III below.

TABLE III

| Method | A | Tramadol | Pentazocine | Morphine |
|---|---|---|---|---|
| Phenylquinone | 1 | 0.67 | 0.77 | 2.5 |
| Writhing Test | 1 | 0.25 | 0.31 | 1.6 |
| Tooth Pulp Nociception Test | 1 | 0.74 | 0.82 | 6.2 |
| | 1 | 0.9 | 0.59 | 2.5 |
| Bradykinin Nociception Test | 1 | 0.03 | 0.5 | 0.66 |
| | 1 | — | 0.34 | 0.45 |
| AgNO$_3$ Arthritis Test | 1 | 0.41 | 0.7 | 8.8 |
| | 1 | 0 | 0.78 | 4.2 |

The values in upper columns and lower columns are calculated from ED$_{50}$ and inhibition (%) in a low dose, respectively.

The analgesic activity in a low dose of Test compound A of the invention is stronger than tramadol and pentazocine. It appears that this fact is of great advantages to medical treatment.

Judging from the analgesic activities in electric stimuli test and tooth pulp nociception test, it can be said that the compounds of the invention are centrally acting analgesics. Therefore, tests for dependence were performed.

(A) Antagonism by levallorphan

In electric stimuli test in mice, administration of levallorphan (narcotic antagonist) did not influence the analgesic activity of Test compound A or C, but reduced that of tramadol.

(B) Mouse jumping test

In mouse jumping test, administration at a lethal dose of Test compound A, B or C did not cause any jumping symptom, but that of tramadol caused to a slight degree.

(C) Body weight change test in rats

In body weight change test in rats, the body weight was not reduced by withdrawal of Test compound A or C or by alternative administration of levallorphan. On the other hand, the body weight was remarkably reduced by codeine. Test compounds A and C had not compensatory adjustment against codeine in cross dependency test, but tramadol had the compensatory adjustment when administered at a 12 hour interval.

(D) Tolerance test

Continuous administration of Test compound A or C did not cause a significant decrease of effects, and did not show a cross tolerance against codeine. Codeine caused a clear tolerance.

(E) Activity on central nervous system

Test compound A showed weak suppression of spontaneous locomotor activity, muscle relaxant activity and reserpine potentiating activity. Test compound B did not show practically such activities.

From the above results of various pharamacological tests, the compounds of the present invention were concluded to belong to the category of non-narcotic, centrally acting analgesics. And further, the following tests were performed.

(F) Effect on the various evoked potentials in central nervous system

Male Wistar rats, weighing 300–350 g, were used under ethyl ether anesthesia. The trachea and femoral vein were cannulated for artificial respiration and drug injection, respectively. Immobilization of the rat was maintained by gallamine thioethiodide (10 mg/kg) given intravenously every one hours. All wound edges were infiltration with carbocaine hydrochloride. The experiments began after at least 2 hours had elapsed from discontinuance of ether anesthesia. The COR (somatosensory cortex) evoked potentials by VP (neucleus ventralis posterior thalamus) stimulation (VP - COR evoked potential) were recorded from somatosensory cortex, through a silver electrode applied directly to the cortex. In order to record VP and MRF (midbrain reticular formation) evoked potentials by sciatic nerve stimulation or AMY (amygdala) and SEP (septum) evoked potentials by HIP (hippocampus) stimulation, bipolar stainless steel electrodes were stereotaxically placed into the VP, MRF, AMY, SEP and HIP. The stimuli were delivered to various sites every 2 seconds from a stimulation and consisted of 0.1 msec rectangular pulses (twice threshold intensity). The evoked responses were visualized on an oscilloscope. All records were made up of 20 superimposed tracings. The results are summarized in Table IV.

TABLE IV

| Test Compound | Dose mg/kg i.v. | Amplitude of Evoked Responses (stimulus site-record site) | | |
|---|---|---|---|---|
| | | VP-COR | HIP-AMY | HIP-SEP |
| A | 5 | — | — | — |
| | 10 | ↘ | — | — |
| | 25 | ↓(−) | — | — |
| C | 5 | — | — | — |
| | 10 | ↑ | — | — |
| | 25 | ↑(−) | — | — |
| Morphine | 2.5 | — | ↑ | — |
| | 5 | ↘ | ↑ | — |
| | 10 | ↓(+) | ↑(+) | ↑(+) |
| Pethidine | 5 | — | ↑ | — |
| | 10 | ↘↑(+) | — | — |
| | 25 | ↓(+) | — | — |
| Aminopyrine | 10 | — | — | — |
| | 25 | ↑ | — | — |
| | 50 | ↑(−) | — | — |
| Tramadol | 5 | — | — | — |
| | 10 | ↗ | — | — |
| | 25 | ↑(−) | — | — |

↑ : Facilitation
↓ : Inhibition
↗ or ↘ : Slight change
— : No change
(+), (−) : Levallorphan antagonism Although the previous pharmacological studies had demonstrated that the compounds of the invention act on the central nervous system as morphine acts, the results in Table IV suggest a difference between the compounds of the invention and morphine. Test compound A reduced the amplitude of the VP - COR evoked potential, but in contrast to the morphine levallorphan did not antagonize the response produced by this compound. Moreover, unlike morphine, Test compound A had no effect on the HIP - AMY and HIP - SEP evoked potentials. From the aspect, the action of this compound differs from that of morphine.

(H) Effect on the aggressive-defense reaction produced by electrical stimulation at the ventro-medial hypothalamus of cats The electrical stimulation of the hypothalamus in cats can bring about threatening and attack behaviours, and stable responses are elicited by stimulation of areas in and close to the ventro-medial hypothalamus by the method described by B. L. Baxter in "Experimental Neurology", 19, 412–432 (1967) and R. Kono et al. in "Neurosciences (Japanese Journal of The Neurosciences Research Association)", 4, 54–55 (1978). The latter used the double-walled cannula method which permitted electrical and chemical stimulation at the same locus in brain. H. Nakao et al. in "Integrative Control Functions of the Brain", vol. II, Kodansha, Tokyo/Elsevier, Amsterdam, 1979, pp. 332–334, demonstrated that glycine, not γ-aminobutyric acid, is possibly an inhibitory transmitter in the regulation of the aggressive-defense reaction. Similar studies have been done using serotonin by L. H. Allikmets in "Pavlov Journal of High Nervous Activity", 22, 597–602 (1972) and using chlorpromazine, haloperidol, pentobarbital and diazepam by H. Maeda in "Folia Psychiatrica et Neurologica Japonica", 30, 539–546 (1976).

Double-walled cannulae were chronically implanted in the ventro-medial hypothalamus of natural docile cats, which produced threatening responses (e.g. growling, hissing, ear-flattening or pupil-dilatation) at the relatively low stimulus intensity (i.e. 5 V by 60 Hz alternating constant voltage supplier, ampere 100–300 μA, 1 min. duration). Stimulation of high intensity evoked retreat or directed attack behaviour against the experimenter.

Test compound B ($10^{-6}$ g) dissolved in saline was injected through the double-walled cannula in a 0.5 μl volumn in 10 minutes and electrical current was gradually increased at 10 μA intervals until threatening and rage behaviours appeared. The threshold of current was raised for 60 minutes and diminished. For comparison $10^{-5}$ g of morphine hydrochloride dissolved in saline was also injected as above, but the threshold of responses was somewhat lowered. Alternatively 30 mg/kg of Test compound B was injected subcutaneously. The threshold of responses was raised over 2 hours, and the cat did not show rage behaviour with provocation by the experimenter. During this experiment the breathing of the cat was normal.

The typical results are summarized in Table V. The standard electric current exhibited the number of 100.

TABLE V

| Time (min) | Compound B $10^{-6}$ g in brain | | | Morphine $10^{-5}$ g in brain | | | Compound B 30 mg/kg s.c. | | |
|---|---|---|---|---|---|---|---|---|---|
| | 0 | 5 | 20 | 0 | 5 | 20 | 0 | 70 | 110 |
| Ear-flattening | 100 | 200 | 200 | 100 | 100 | 95 | 100 | 120 | 105 |
| Growling | 100 | 200 | — | 100 | 100 | 100 | 100 | 177 | 184 |
| Pupil dilatation | 100 | 200 | — | — | — | — | — | — | — |
| Retreat with provocation | 100 | 180 | — | 100 | 92 | 88* | 100 | 142 | 127 |

—: not observed
*attack response occured

Test compound B clearly suppressed the threatening, rage and retreat reactions which evoked by electrical stimulation of the ventro-medial hypothalamus. This fact suggests that the compounds of the invention may block physiologically discharges from hypothalamus to limbic system and suppress the hyperemotionality by pain, etc. Similar responses were observed in chlorpromazine, pentobarbital and diazepam in directed attack but the inhibition of threatening and rage reactions of these was less active.

The compounds of this invention are quite new centrally acting analgesics which strongly suppress inflammatory pain (antibradykinin activity) and do not show the acquisition of dependence, and the activity of the compounds are not antagonized by levallorphan.

(I) Acute toxicity

TABLE VI

| Test Compound | $LD_{50}$ mg/kg rats | | |
|---|---|---|---|
| | p.o. | s.c. | i.p. |
| A | 450 | 300 | 150 |
| B | 1200 | 500 | 150 |
| C | 900 | 700 | 150 |
| D | 500 | 450 | 180 |
| Tramadol | 228 | 300 | 150 |
| Pentazocine | 1100 | 270 | — |
| Morphine | 400 | 750 | 100 |
| Aminopyrine | 1050 | — | 248 |

In view of various tests including those mentioned above, the compounds of the invention represented by formula (I), in base or salt form, can be safely administered as analgesics in the form of a pharmaceutical preparation with a suitable and conventional pharmaceutically acceptable carrier, without adversely affecting the patients.

The pharmaceutical preparations can take any conventional form such as tablets, capsules, granules, powders or injectable solutions.

The following is an example of formulations when a compound of the invention is administered for pharmaceutical purposes.

Tablets (60 mg) are prepared from the following compositions:

| | |
|---|---|
| Compound I or its salt | 60 mg |
| Lactose | 100 mg |
| Cornstarch | 40 mg |
| Microcrystalline cellulose | 17 mg |
| Methyl cellulose | 1.5 mg |
| Magnesium stearate | 1.5 mg |
| | 220 mg |

The daily dose of compound (I) or a salt thereof for human adults usually ranges from about 30 mg to about 3000 mg for oral administration and from about 10 mg to about 1000 mg for parenteral administration, in single or multiple dose, but it may vary depending upon the age, body weight, and/or severity of the conditions to be treated as well as the response to the medication.

The present invention will be better understood from the following examples, but they are not to be construed as limiting the present invention.

EXAMPLE 1

A mixture of 25 g of cinnamyl chloride, 35 g of 1-(4-piperidyl)-hydrouracil and 20 g of potassium carbonate in 300 ml of 60% ethanol is stirred at room temperature for 3 hours and then refluxed for one hour. The solvent is then distilled off, and the residue is shaken with 200 ml of toluene and 100 ml of water. The toluene layer is washed with water and dried over potassium carbonate, and alcoholic hydrochloric acid is added. The precipitated crystals are collected by filtration and recrystallized from ethanol to give 1-(1-cinnamyl-4-piperidyl)-hydrouracil hydrochloride as white crystals, m.p. 286° C.,58% yield.

EXAMPLE 2

A mixture of 25 g of cinnamyl chloride, 35 g of 1-(4-piperidyl)-3-methyl-hydrouracil and 20 g of potassium carbonate in 300 ml of methyl isobutyl ketone is stirred at room temperature for 3 hours and then at 100° C. for 6 hours. The solvent is then distilled off, and the residue is shaken with 200 ml of toluene and 100 ml of water. The toluene layer is washed with water and dried over potassium carbonate, and alcoholic hydrochloric acid is added. The precipitated crystals are collected by filtration and recrystallized from ethanol to give 1-(1-cinnamyl-4-piperidyl)-3-methyl-hydrouracil hydrochloride as white crystals, m.p. 264°-266° C., 68% yield.

EXAMPLE 3

A mixture of 4.0 g of 1-phenethyl-4-aminopiperidine and 2.1 g of acrylamide in 20 ml of methanol is refluxed for 5 hours. The methanol is then distilled off, and the residue (crude 3-(1-phenethyl-4-piperidyl)-propionamide) is dissolved in 30 ml of chloroform. The solution is washed with water and dried over anhydrous magnesium sulfate. Triethylamine (3 g) is added to the chloroform solution whereupon 2 g of phosgene is introduced over a period of 30 minutes. The resulting mixture is stirred at room temperature for one hour and then under reflux for one hour. Ethanolic hydrochloric acid is added to the reaction mixture. The precipitated crystals are collected by filtration, washed with ethanol and recrystallized repeatedly from 80% ethanol to give 3.8 g of 1-(1-phenethyl-4-piperidyl)-hydrouracil hydrochloride as white crystals, m.p. 318° C.

EXAMPLE 4

1-Phenethyl-4-aminopiperidine (10 g) is mixed with 5 g of ethyl acrylate in 100 ml of ethanol under cooling. The temperature is raised gradually, and the mixture is refluxed for one hour and then cooled to 10° C. Methyl isocyanate (3 g) is added, and the resulting mixture is stirred for 30 minutes and then refluxed for 30 minutes. After cooling 20 g of 30% ethanolic hydrochloric acid is added to the reaction mixture, and the whole is refluxed for 1.5 hours and then cooled. The precipitated crystals are collected by filtration and recrystallized from methanol to give 1-(1-phenethyl-4-piperidyl)-3-methyl-hydrouracil hydrochloride as white crystals, m.p. 311° C. (decomposition).

While the invention has been described in detail and with reference to specific embodiments thereof, it will be apparent to one skilled in the art that various changes and modifications can be made therein without departing from the sprit and scorp thereof.

What is claimed is:

1. A hydrouracil compound of the formula:

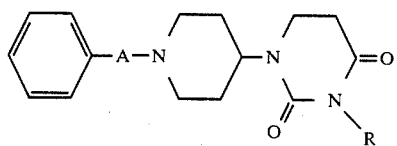

or a pharmaceutically acceptable acid addition salt thereof, wherein A represents —CH=CH—CH$_2$— or —CH$_2$CH$_2$—, and R represents hydrogen or methyl.

2. The compound of claim 1: 1-(1-cinnamyl-4-piperidyl)-3-methyl-hydrouracil.

3. The compound of claim 1: 1-(1-cinnamyl-4-piperidyl)hydrouracil.

4. The compound of claim 1: 1-(1-phenethyl-4-piperidyl)-3-methyl-hydrouracil.

5. The compound of claim 1: 1-(1-phenethyl-4-piperidyl)hydrouracil.

6. A pharmaceutical composition comprising the compound of claim 1 in combination with a pharmaceutically acceptable inert carrier, said compound being present in a therapeutically effective amount.

* * * * *